United States Patent
Gramnäs

[19]

[11] Patent Number: 5,921,358
[45] Date of Patent: Jul. 13, 1999

[54] ROTATION DAMPER IN A TOGGLE JOINT PROSTHESIS

[75] Inventor: Finn Gramnäs, Kinna, Sweden

[73] Assignee: Gramtec Innovation AB, Kinna, Sweden

[21] Appl. No.: 08/817,317

[22] PCT Filed: Sep. 29, 1995

[86] PCT No.: PCT/SE95/01106

§ 371 Date: Apr. 7, 1997

§ 102(e) Date: Apr. 7, 1997

[87] PCT Pub. No.: WO96/10969

PCT Pub. Date: Apr. 18, 1996

[30] Foreign Application Priority Data

Oct. 7, 1994 [SE] Sweden .................................. 9403406

[51] Int. Cl.[6] ............................. A61F 2/64; F16D 57/02
[52] U.S. Cl. ........................... 188/294; 188/293; 623/39; 623/44
[58] Field of Search ..................................... 188/266, 268, 188/290–296, 322.5; 623/44, 46, 59

[56] References Cited

U.S. PATENT DOCUMENTS

| | | | |
|---|---|---|---|
| 3,801,990 | 4/1974 | Helfet | 623/39 |
| 3,851,337 | 12/1974 | Prahl | 623/43 |
| 3,864,758 | 2/1975 | Yakich | 623/40 |
| 4,112,522 | 9/1978 | Dadurian et al. | 623/39 |
| 4,206,517 | 6/1980 | Pappas et al. | 623/23 |
| 4,318,191 | 3/1982 | Tepic | 623/39 |
| 4,919,660 | 4/1990 | Peilloud | 623/20 |
| 5,085,665 | 2/1992 | Radocy et al. | 623/57 |
| 5,171,325 | 12/1992 | Aulie | 623/43 |
| 5,314,498 | 5/1994 | Gramnas | 623/39 |
| 5,695,526 | 12/1997 | Wilson | 623/49 |
| 5,704,945 | 1/1998 | Wagner et al. | 623/44 |

*Primary Examiner*—Chris Schwartz
*Attorney, Agent, or Firm*—Gardner, Carton & Douglas

[57] ABSTRACT

A rotation damper for toggle joints prosthesis (1) that is arranged for swing phase control of the prosthesis, and incorporates a housing having at least one clamber (13) with a damping medium disposed therein is disclosed. The chamber is arranged so that the damping medium is displaced through a restriction (14a) with a swing motion of at least one pivot axle (6) in the prosthesis. The damping medium is a visco-elastic compound, having an ability to exert a bigger resistance at rapid motion processes as compared to slower processes.

13 Claims, 4 Drawing Sheets

ROTATION DAMPER IN A TOGGLE JOINT PROSTHESIS

BACKGROUND OF THE INVENTION

The present invention refers to a rotation damper for a so called swing phase control at toggle joint prosthesis. This swing phase control provides a dampening of the forward swing motion of a limited swing angle, which occurs when the lower part of the toggle joint prosthesis, after a finished step, is moved forward rapidly for initiation of the next step. Without such a rotation dampening of the joint the prosthesis bearer will get a bumpy walk, which is not only unnatural, but which also causes increased stress on the prosthesis and body parts cooperating therewith.

For such rotation dampening of toggle joint prostheses in more simple cases earlier have been used dampening rubber blocks and at more sophisticated embodiments, more or less complex hydraulic systems, with valves and pistons of rather small dimensions, which were manufactured with high precision. This means that such earlier rotation dampers have been expensive components, which have often meant intricate sealing problems, in order to prevent the hydraulic fluid from leaking out.

SUMMARY OF THE INVENTION

The purpose of the present invention is to provide such a rotation damper for a toggle joint prosthesis, which eliminates the above mentioned problems and provides a leak-proof, reliable mechanism, which is inexpensive to produce and can be manufactured in different embodiments. This has been achieved in that the rotation damper has been given the features defined in the accompanying claims.

BRIEF DESCRIPTION OF THE DRAWINGS

Hereinafter the invention will be further described with reference to an embodiment schematically shown in the accompanying drawings.

DETAILED DESCRIPTION OF THE PREFERRED EMBODIMENTS

Figure 1:
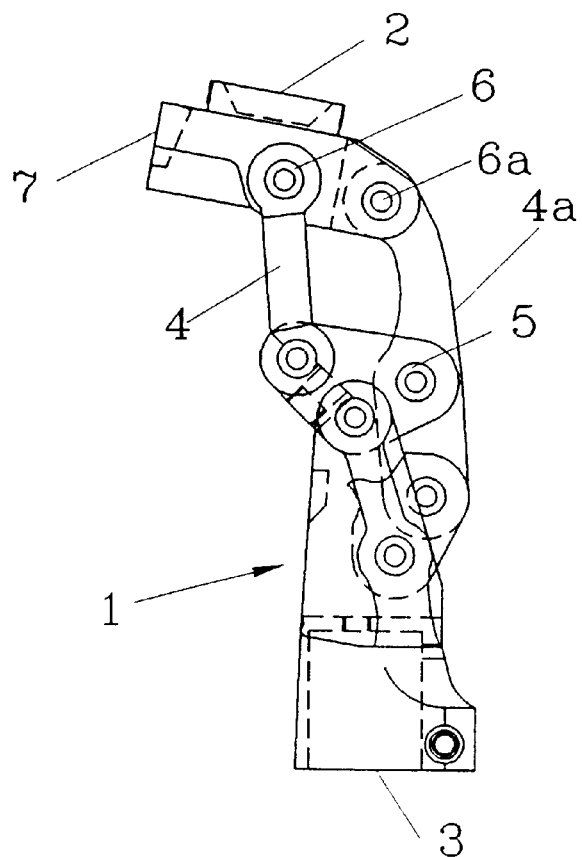
FIG. 1 shows in a side view a non-limiting embodiment of a toggle joint prosthesis, which can be equipped with a rotation damper according to the invention.

FIG. 1 shows in a side view a toggle joint prosthesis 1, which, without being a limitation for the invention, can be an appropriate mechanism for application of the rotation damper according to the invention. The prosthesis incorporates an upper attachment 2 and a lower attachment 3. The attachments 2 and 3 are mutually articulated by means of a system of links 4, 5, pivotably journalled to each other, and which permit that the upper and lower attachments 2, 3 can be angled relative to each other, so that the prosthesis gives a very natural walking pattern. Such a prosthesis is known e.g. from U.S. Pat. No. 5,314,498, and it therefore will not be described in detail in this specification.

Figure 2:
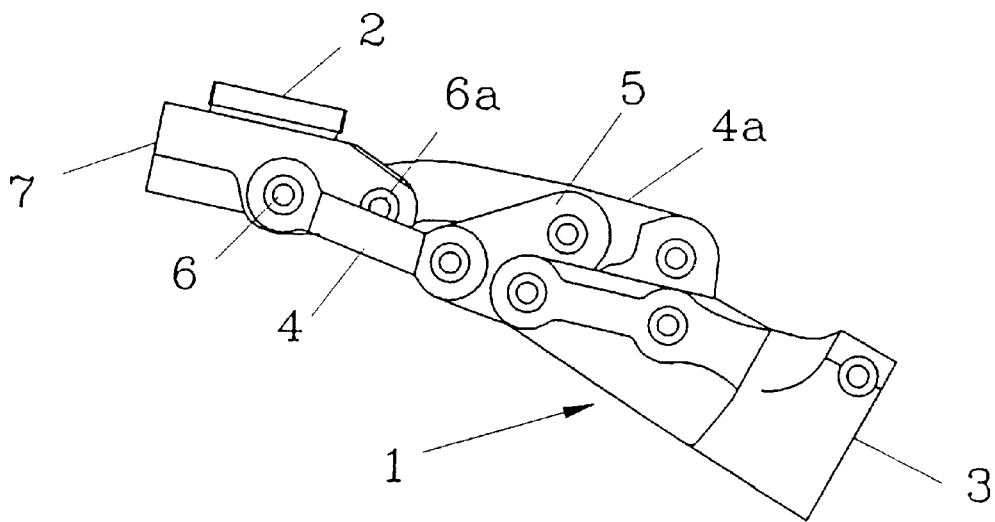
FIG. 2 is a corresponding view of the toggle joint prosthesis according to FIG. 1 with the joint in a rearwardly extended position.
Figure 3:
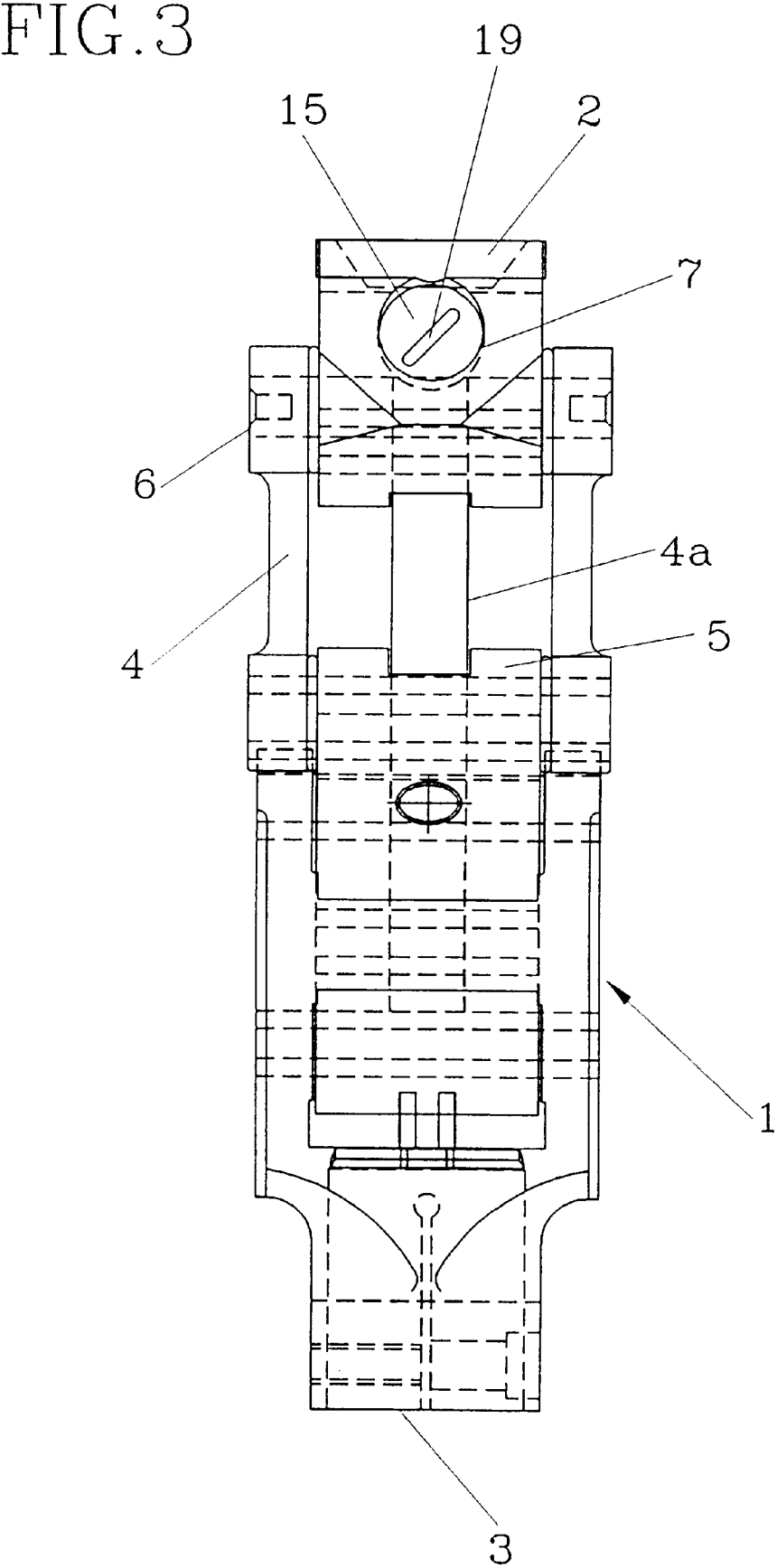
FIG. 3 shows the toggle joint prosthesis according to FIG. 1 in a view straight from the front.

The forward pair of links 4 is articulately attached to the upper attachment 2 via a pivot 6, whereas a rearward link 4a, in the same manner is articulated to the upper attachment in a pivot 6a. As can be seen from FIG. 2, the prosthesis is shown with the lower part in a rearwardly bent position, i.e., the link 4 at the swing motion has moved about the pivot 6. For this movement, and also during the consecutive forward swing motion to the stretched knee joint position it is required to promote a dampening device for reducing the stresses upon the joint system. For this purpose a rotation damper according to the invention can preferably be provided in this joint 6. The maneuvering of the rotation damper is effected through an opening 7 at the forward part of the upper attachment.

Figure 4:
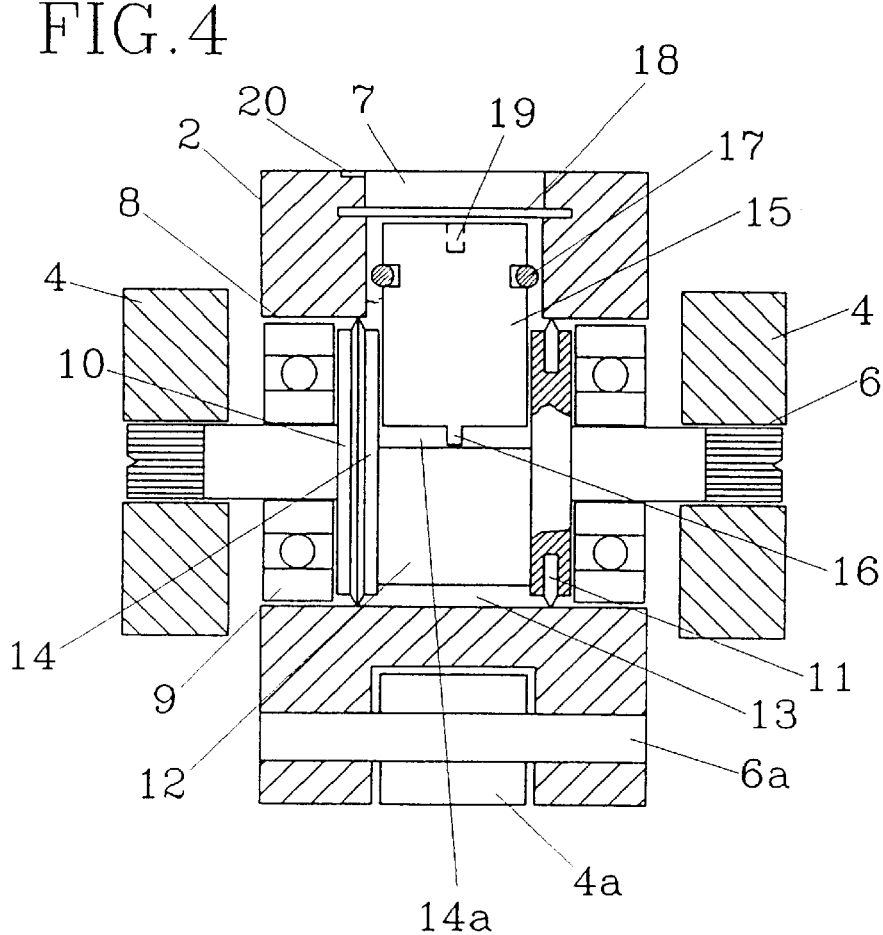
FIG. 4 shows schematically a cross section through a portion of the toggle joint prosthesis according to FIG. 1, with the rotation damper forming part thereof in a completely open position.
Figure 5:
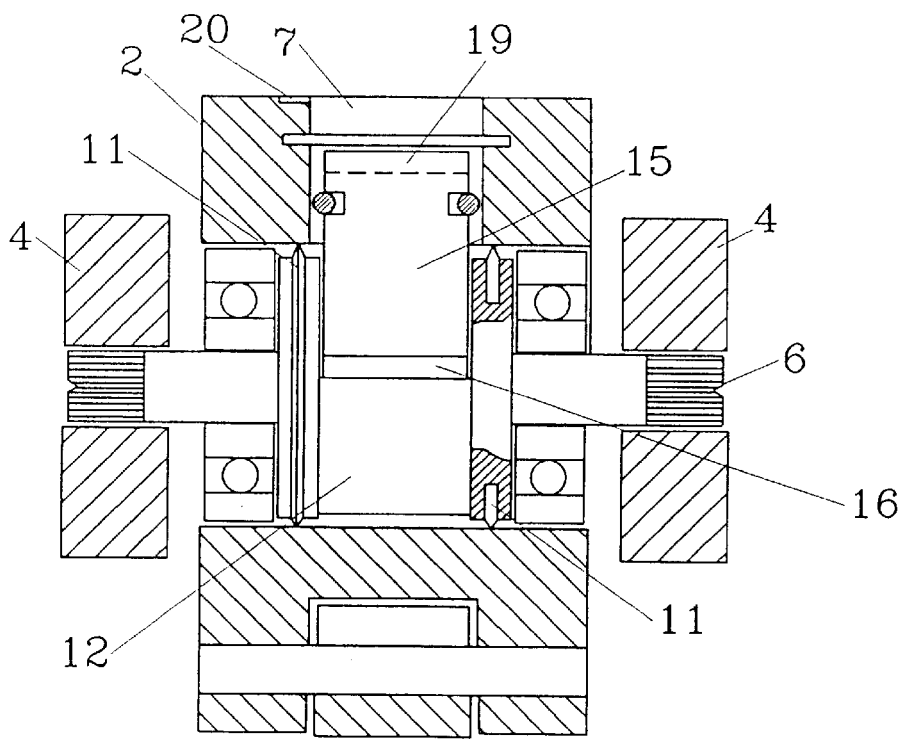
FIG. 5 is a view corresponding to FIG. 4 but with the rotation damper according to the invention in a completely closed position.

FIGS. 4 and 5 show schematically in cross section the upper attachment 2 with its links 4 and 4a, respectively, which are equipped with pivot axles 6 and 6a, respectively. In the embodiment shown thereby only the forward joint 6 is designed as a rotation damper according to the invention. The pivot axle 6 is, via splines, non-rotationally connected to the links 4, which are arranged one on each side of the housing formed by the upper attachment 2, which has a through-opening 8, through which the pivot axle 6 extends, supported in ball bearings 9. Inside the position of the ball bearings 9 the pivot axle 6 is equipped with radial flanges 10, which support sealing means 11, which seal off the space inside thereof to a chamber 13. Between the two flanges 10 the pivot axle 6 is equipped with a wing 12, which extends over the entire length of the chamber and is arranged on a portion 14 of the pivot axle 6, and has a smaller diameter than the rest of the pivot axle.

In the housing formed by the attachment 2, as mentioned above, there is also provided an opening 7, which extends as a cylindrical channel from the front part of the attachment and opens in the chamber 13. In the channel 7 there is inserted an adjustment device cooperating with the pivot axle wing 12 and being in the form of cylindrical tap 15, which, at its end projecting into the channel, is provided with a diametrically extending ridge 16. The cylindrical surface of the tap is sealed off against the wall of the channel, e.g. by means of a circumferential sealing ring 17, positioned in a groove. The tap 15 is secured in its axial position in the channel 7 by means of a stop ring 18 inserted in a groove in the channel wall. The tap 15 however is rotatably arranged in the channel and, in its outwardly positioned end, has a grip 19 for a tool, in the embodiment shown a diametrical groove for a screwdriver. The tap can be rotated thus in the channel 7, that its ridge 16 can be turned stepless from the position shown in FIG. 4 with its longitudinal direction perpendicularly against the axial extension of the chamber 13 and to the position shown in FIG. 5, wherein the longitudinal direction of the ridge coincides with the axial extension of the chamber. In this manner it is possible to set a flow section area between completely open, according to FIG. 4 and completely closed according to FIG. 5.

In the outer side of the housing and adjoining the opening of the channel 7 there is preferably provided a marking 20, which can act as an index for establishing the current rotational angle of the tap, and thereby the position for the ridge 16 and the size of the slot 14*a*, by comparison with the groove 19 provided diametrically in the tap.

In the manner now described, there has been created a simple rotational damper, which shall operate with a dampening medium. During the swinging motion of the links 4, the dampering medium is caused to move through the slot 14*a* formed between the portion 14 of the pivot axle and the ridge 16 on the tap 15 axel 6.

By using a visco-elastic compound as a damping medium instead of the usual hydraulic oil, a number of advantages are achieved. An appropriate visco-elastic compound is a boron-siloxane-elastomer, marketed by the company Wacker Kemi AB, Stockholm, Sweden, under the trade name "HÜPFENDER KITT", as a therapeutic toy or a kneading lump, etcetera.

An advantage with such a visco-elastic compound is that it does not require sealing accuracy, i.e. the cooperating sealing surfaces need not have particularly accurate tolerances, which means lower manufacturing costs and a lower risk for leakages. The compounds used function so, that the compound tending to penetrate out through the sealing slot under rapid swing motions will pull itself into the sealed off space, after the motion has ceased. Another advantage with these types of visco-elastic compounds, which is very important in this context, is that when heavily kneaded, i.e. at a rapid swing motion of the links 4 and therefore of the wing 12 on the pivot axle 6, will exert a substantially bigger flow resistance as compared to a slow motion.

From this it is also evident that a reduced flow through the restriction 14*a*, caused by the tap 15 and its diametrical ridge 16, which increases the flow velocity, means a more forceful kneading of the compound and thereby a bigger resistance to the rotational motion.

However, the invention is not limited to this visco-elastic compound, but other corresponding compounds with similar properties can also be used.

Figure 6:
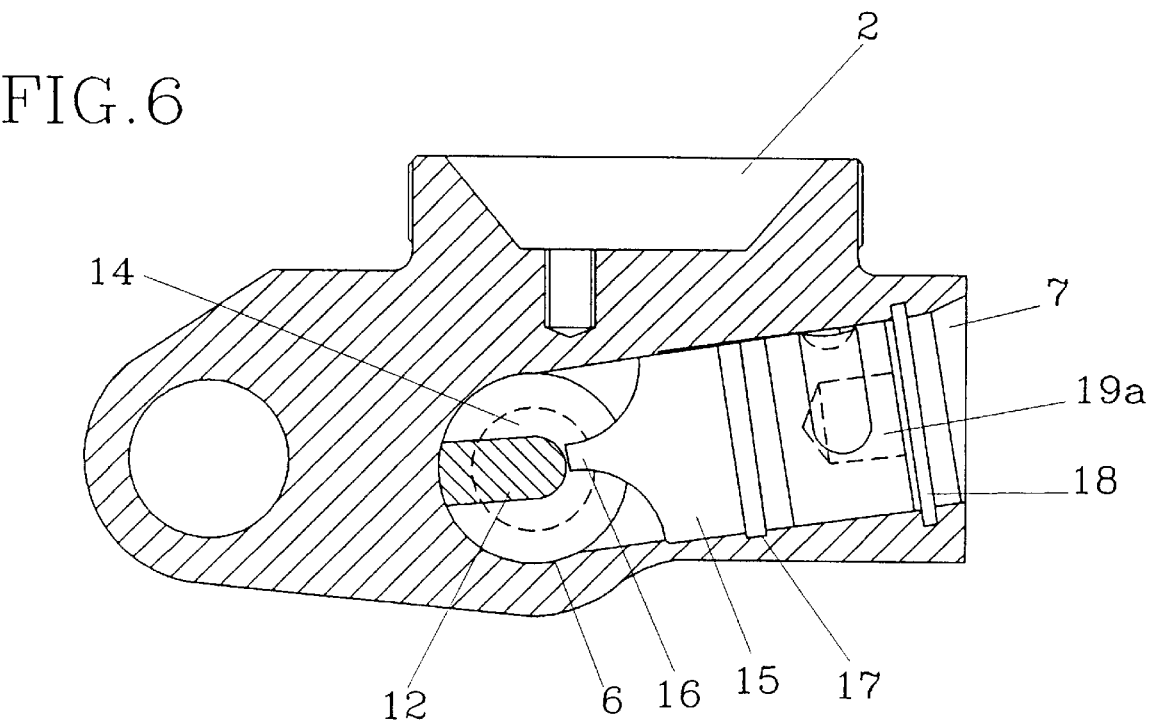
FIG. 6 shows another section through an upper attachment forming part of the toggle joint prosthesis with a rotation damper provided therein.

In FIG. 6 is shown in cross section the upper attachment 2 with the members forming part thereof and belonging to the rotation damper according to the invention, i.e. the pivot axle 6 with its wing 12 and the cylindrical tap 15 and its forward diametrical ridge 16 intended for adjusting the flow area. The only difference as compared to the design according to FIGS. 4 and 5 is that the tap 15 in its outward surface has a tool grip 19*a* in the form of a hexagonal recess. In the shown position of the tap 15 the flow area is completely closed, as the ridge 16 extends axially along the extension of the wing 12 and therefore has sealed off the through-flow slot completely.

Figure 7:
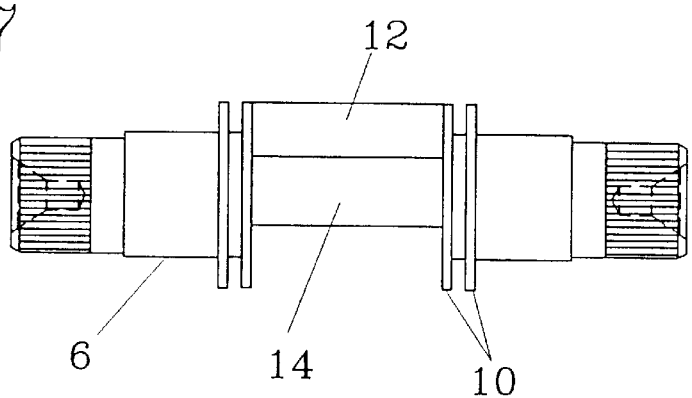
FIG. 7 shows in side view a pivot axle forming part of the rotation damper according to FIG. 6.

In FIG. 7 the pivot axle 6 is shown by itself in side view.

The invention is not limited to the embodiment shown and described in connection therewith, but modifications may occur within the scope of the accompanying claims.

Thus it is not necessary that the visco-elastic rotation damper according to the invention has a wing attached to the pivot axle, and which at the pivot motion of the joint tends to displace the visco-elastic compound through a flow slot, the size of which is adjustable in a manner such as described, but the swing motion may be transferred in other manners into a displacement of a visco-elastic compound through a restrictable opening, e.g. by means of a piston arrangement.

The tap 15 may furthermore, e.g. instead of, or as a complement to the ridge have inserted therein an adjustable, restricted non-return valve, for setting the resistance individually in both directions.

The embodiment shown in the accompanying drawings and described in connection thereto however is considered as a well operating and from cost aspects advantageous solution.

I claim:

1. A dampening device for reducing stresses on a joint of a toggle joint prosthesis, wherein the toggle joint prosthesis has at least one pivot axle at a joint, the dampening device comprising:
    a housing;
    a chamber formed within the housing;
    a damping medium contained within the chamber wherein the damping medium is a visco-elastic compound; and
    a restriction provided in the chamber wherein a swing motion of the pivot axle displaces the dampening medium through the restriction.

2. The dampening device according to claim 1 further comprising a projecting wing disposed in the chamber wherein the projecting wing is adapted to be connected to the pivot axle, and the restriction being in the form of a slot wherein the wing displaces the damping medium through the slot with a limited flow area.

3. The dampening device according to claim 2 wherein the size of the slot is adjustable.

4. The dampening device according to claim 3 wherein the slot is adjustable between a completely open position and a completely closed position.

5. The dampening device according to claim 3 further comprising a cylindrical tap to adjust the size of the slot wherein the cylindrical tap is operable from outside the device.

6. The dampening device according to claim 3 further comprising a ridge to adjust the size of the slot wherein the ridge is operable from outside the device.

7. The dampening device according to claim 1 wherein the chamber includes at least one cylindrical bore and the pivot axle extends through the bore and wherein the device further comprising:
    at least one seal to axially seal the dampening medium in the chamber; and
    a wing disposed in the chamber and adapted to be connected to the pivot axle wherein the wing is directed radially through the chamber and extends axially between the seals.

8. A dampening device for reducing stress on a joint of a toggle joint prosthesis, wherein the toggle joint prosthesis has at least one pivot axle at a joint, the dampening device comprising:
    a housing;
    a chamber formed within the housing having a portion of the pivot axle disposed within the chamber and having a slot disposed within the chamber;
    a cylindrical tap projecting through the channel and having a diametrically extending ridge arranged to engage the pivot axle within the chamber and wherein the ridge can vary the size of the slot by rotation of the tap;
    a damping medium contained within the chamber wherein the damping medium is a visco-elastic compound and the damping medium is displaced through the slot by a swing motion of the pivot axle.

9. The dampening device according to claim 8 wherein the tap is secured in its axial position in the channel by a stop wing.

10. The dampening device according to claim 8 further comprising:

a key grip provided on the tap; and a mark on the outside of the chamber wherein the key grip is arranged to indicate the position of the ridge against the mark and thereby the momentary flow of the damping fluid through the slot.

11. The dampening device according to claim 8 further comprising a projecting wing disposed in the chamber wherein the projecting wing is adapted to be connected to the pivot axle and the projecting wing displaces the damping medium through the slot.

12. The dampening device according to claim 8 wherein the slot can vary between a completely open position and a completely closed position.

13. The dampening device according to claim 8 wherein the chamber includes at least one cylindrical bore and the pivot axle extends through the bore and wherein the device further comprising:

at least one seal to axially seal the damping medium in the chamber; and a wing adapted to be connected to the pivot axle wherein the wing is directed radially through the chamber and extends axially between the seals.

* * * * *

UNITED STATES PATENT AND TRADEMARK OFFICE
CERTIFICATE OF CORRECTION

PATENT NO. : 5,921,358
DATED : 13 July 1999
INVENTOR(S) : Gramnas

It is certified that error appears in the above-identified patent and that said Letters Patent is hereby corrected as shown below:

Column 3, Line 8, between "15" and "axel 6." insert --by the wing rigidly connected to the pivot -- therefor;

Signed and Sealed this

Eleventh Day of January, 2000

Attest:

Q. TODD DICKINSON

Attesting Officer

Acting Commissioner of Patents and Trademarks